(12) United States Patent
Moreno et al.

(10) Patent No.: US 8,073,709 B2
(45) Date of Patent: Dec. 6, 2011

(54) CPT PRICING FROM MEDPAR DATA

(75) Inventors: Paul W. Moreno, Alpharetta, GA (US); Stephen K. Barclay, Woodstock, GA (US); Yuri P. Kobylniak, Marietta, GA (US)

(73) Assignee: 3M Innovative Properties Company, Saint Paul, MN (US)

( * ) Notice: Subject to any disclaimer, the term of this patent is extended or adjusted under 35 U.S.C. 154(b) by 915 days.

(21) Appl. No.: 11/744,556

(22) Filed: May 4, 2007

(65) Prior Publication Data

US 2008/0275724 A1  Nov. 6, 2008

(51) Int. Cl.
*G06Q 10/00* (2006.01)
*G06Q 50/00* (2006.01)

(52) U.S. Cl. .............................. 705/2; 705/3
(58) Field of Classification Search ............... 705/2
See application file for complete search history.

(56) References Cited

U.S. PATENT DOCUMENTS

| | | | |
|---|---|---|---|
| 4,667,292 A | 5/1987 | Mohlenbrock et al. | |
| 4,831,526 A | 5/1989 | Luchs et al. | |
| 5,235,507 A | 8/1993 | Sackler et al. | |
| 5,446,653 A | 8/1995 | Miller et al. | |
| 5,523,942 A | 6/1996 | Tyler et al. | |
| 5,652,842 A * | 7/1997 | Siegrist et al. | 705/2 |
| 6,014,632 A | 1/2000 | Gamble et al. | |
| 6,163,770 A | 12/2000 | Gamble et al. | |
| 6,959,429 B1 | 10/2005 | Hatcher et al. | |
| 2004/0243438 A1 | 12/2004 | Mintz | |
| 2006/0143042 A1 | 6/2006 | Gragg et al. | |

OTHER PUBLICATIONS

Gazelle, Cost-Effectiveness of Hepatic Metastasectomy in Patients With Metastatic Colorectal Carcinoma, Ann Surg. Apr. 2003; 237(4): 544-555.*
Bates, Using diagnoses to describe populations and predict costs, Health Care Financing Review/Spring 2000/vol. 21, No. 3.*
Ross, Introduction to Probability and Statistics for Engineers and Scientists, 2004, Elsevier Academic Press, Third Edition, p. 19-22.*
Gazelle (Cost-Effectiveness of Hepatic Metastasectomy in Patients With Metastatic Colorectal Carcinoma, mailed Jun. 9, 2010).*
Fries, B. E. et al.: "A Comprehensive Payment Model for Short-and Long-Stay Psychiatric Patients." Health Care Financing Review, vol. 15, No. 2, pp. 31-50, (Winter) 1993.
Clauser, S. B. et al.: "Nursing Home Resident Assessment and Case-Mix Classification: Cross-National Perspectives." Health Care Financing Review, vol. 13, No. 4, pp. 135-155, Summer 1992.
Fries, B. E. et al.: "Refining a Case-Mix Measure for Nursing Homes: Resource Utilization Groups (RUG-III)" Medical Care, vol. 32, No. 7, pp. 668-685, 1994.
Williams, B. C., et al.: "Activities of Daily Living and Costs in Nursing Homes." Health Care Financing Review, vol. 15, No. 4, pp. 117-135, Summer 1994.
Schultz, B. M., et al.: "RUG-II Impacts on Long-Term Care Facilities in New York." Health Care Financing Review, vol. 16, No. 2, pp. 85-99, Winter 1994.
Cornelius, E. et al.: "Creating a MEDPAR Analog to the RUG-III Classification System", Health Care Financing Review, vol. 16, No. 2, pp. 101-126, Winter 1994.

(Continued)

*Primary Examiner* — Luke Gilligan
*Assistant Examiner* — Tran Nguyen
(74) *Attorney, Agent, or Firm* — Steven A. Bern

(57) ABSTRACT

Methods and systems for computing what a healthcare organization charged for a procedure, based on analysis of MedPAR data.

16 Claims, 6 Drawing Sheets

OTHER PUBLICATIONS

Proposed Medicare Skilled Nursing Facility Prospective Payment System. Health Care Financing Review, pp. 78-79, 1995 Statistical Supplement.

Hawes, C. et al.: "Reliability Estimates for the Minimum Data Set for Nursing Home Resident Assessment and Care Screening (MDS)." The Gerontologist, vol. 35, No. 2, pp. 172-178, Apr. 1995.

* cited by examiner

| CPT CODE | Count | Charge | 75th Percentile |
|---|---|---|---|
| 11042 | 1 | $ 1,157.00 | $ 775.00 |
| 11042 | 1 | $ 985.00 | |
| 11042 | 7 | $ 775.00 | |
| 11042 | | $ 775.00 | |
| 11042 | | $ 775.00 | |
| 11042 | | $ 775.00 | |
| 11042 | | $ 775.00 | |
| 11042 | | $ 775.00 | |
| 11042 | | $ 775.00 | |
| 11042 | 1 | $ 620.00 | |
| Total | 10 | | |

*Fig. 5A*

| CPT CODE | Count | Charge | Percent |
|---|---|---|---|
| 11042 | 1 | $ 1,157.00 | 10% |
| 11042 | 1 | $ 985.00 | 10% |
| 11042 | 5 | $ 775.00 | 50% |
| 11042 | | $ 775.00 | |
| 11042 | | $ 775.00 | |
| 11042 | | $ 775.00 | |
| 11042 | | $ 775.00 | |
| 11042 | 3 | $ 620.00 | 30% |
| 11042 | | $ 620.00 | |
| 11042 | | $ 620.00 | |
| Total | 10 | | 100% |

*Fig. 5B*

| CPT CODE | Count | Charge | Percent |
|---|---|---|---|
| 11042 | 10 | $ 1,157.00 | 17% |
| 11042 | 12 | $ 985.00 | 20% |
| 11042 | 25 | $ 775.00 | 42% |
| 11042 | 13 | $ 620.00 | 22% |
| *Total* | 60 | | 100% |

*Fig. 5C*

| CPT CODE | Count | Charge | Percent |
|---|---|---|---|
| 11042 | 19 | $ 1,157.00 | 21% |
| 11042 | 25 | $ 985.00 | 28% |
| 11042 | 25 | $ 775.00 | 28% |
| 11042 | 21 | $ 620.00 | 23% |
| *Total* | 90 | | 100% |

*Fig. 5D*

| CPT CODE | Count | Charge | Percent |
|---|---|---|---|
| 11042 | 19 | $ 1,157.00 | 16% |
| 11042 | 31 | $ 985.00 | 27% |
| 11042 | 45 | $ 775.00 | 39% |
| 11042 | 21 | $ 620.00 | 18% |
| *Total* | 116 | | 100% |

*Fig. 5E*

CPT PRICING FROM MEDPAR DATA

BACKGROUND

For a healthcare organization, such as a hospital, competitor pricing information is useful competitive intelligence. One source for such pricing information is MedPAR data, which is based on information reported by healthcare organizations to the government, and thusly made available to the public for a fee. For various reasons, MedPAR data often has several or many charge amounts associated with a particular procedure for a particular healthcare organization.

SUMMARY

In general, the present invention is directed to methods and systems supporting the application of a set of rules to MedPAR data, yielding data indicative of what a healthcare organization actually charges for a procedure. Further, the disclosure is further directed to methods used to commercialize this information.

In one embodiment, the present invention is directed toward a computer-implemented method of determining an actual amount a target healthcare organization charges for a procedure, the procedure associated with a CPT code, the method comprising: accessing MedPAR data defining a plurality of charge amounts charged by the target healthcare organization for the procedure; applying a set of rules to the MedPAR data; and, based on the application of the set of rules, computing a dollar amount the healthcare organization charged for the CPT code associated with the procedure.

In another embodiment, the disclosure is directed toward a system for identifying an actual amount a target healthcare organization charges for a procedure, the procedure associated with a CPT code, the system comprising: a database component operative to maintain records identifying a plurality of amounts the target healthcare organization has charged for the procedure associated with the CPT code; a processor programmed to: retrieve the records from the database component; apply a set of rules to the records; and, based on the application of the set of rules, compute an actual amount charged by the target healthcare organization for the procedure associated with the CPT code.

In another embodiment, the disclosure is directed toward a method of benchmarking at least a portion of a first healthcare organization's chargemaster against a second healthcare organization, comprising: receiving at least a portion of the first healthcare organization's chargemaster, the chargemaster including an amount charged for a procedure associated with a CPT code; applying a set of rules to MedPAR data, the MedPAR data including data defining a plurality of amounts the second healthcare organization has charged for the procedure associated with the CPT code, the set of rules determining an actual charge amount, among the plurality of amounts; and, providing a report to the first healthcare organization, the report including the amount charged for the procedure associated with the CPT code by the first healthcare organization against the actual charge amount of the second healthcare organization.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 5A, 5B, 5C, 5D, and 5E show examples of the application of the logic shown in various steps in FIG. 4.

DETAILED DESCRIPTION

Figure 1:
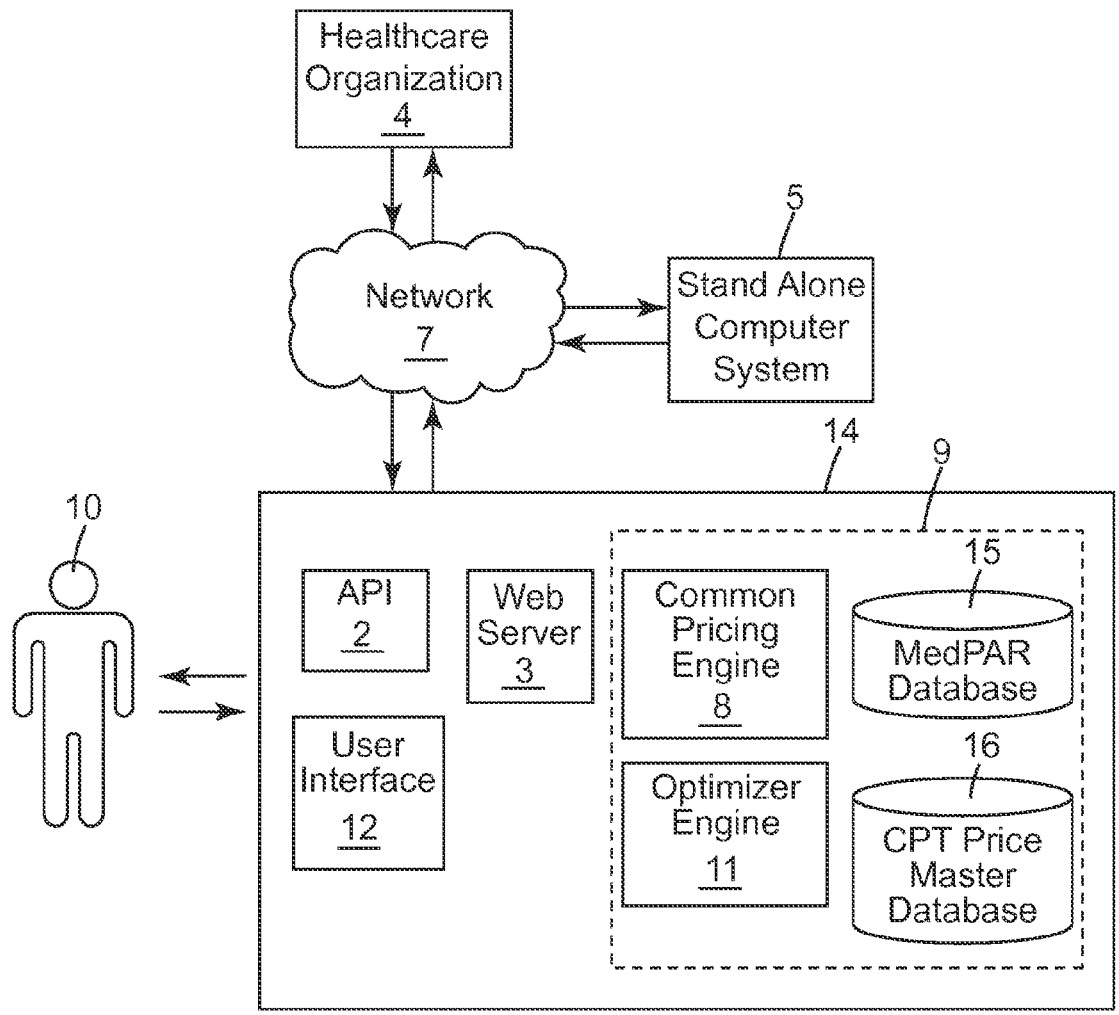
FIG. 1 is a diagram showing an exemplary embodiment of CPT pricing system in accordance with the present invention.

A patient's encounter with a healthcare organization (for example a hospital or skilled nursing facility) is often documented by the healthcare organization using pre-defined codes that represent services provided to the patient. One such code base is marketed by the American Medical Association under the trade designation Current Procedure Terminology, or CPT. CPT codes describe or define services rendered to a patient. Once a patient's encounter with a healthcare organization has been appropriately described by CPT codes, the codes may be used for billing purposes, by cross referencing particular codes against a chargemaster. A chargemaster is a table that defines prices for particular CPT codes. Once the CPT codes have been cross-referenced with prices, hospitals can generate and submit bills to payment organizations, which in turn may have their own chargemaster-type tables which define what the payment organization will in fact pay for procedures associated with particular CPT codes.

Abstracts of the CPT-coded bills submitted to Medicare for payment are made available to the public via a product offering called MedPAR. MedPAR data refers to Medicare Provider Analysis and Review dataset, which is maintained by, and available from, the Centers for Medicare and Medicaid Services (http://www.cms.hhs.gov) for a nominal fee.

MedPAR data is typically purchased by companies that analyze it and make reports or views of the data available, usually for a fee, to healthcare organizations, researchers, etc. Researchers might use the MedPAR data, or various abstracts of it, to research chronic disease prevalent in the elderly population (cancer, heart disease, diabetes, etc.), or for mortality studies. Healthcare organizations, on the other hand, may be interested in reports based on the MedPAR data that show information about competitors or peer companies. For example, with the MedPAR data it is possible to get a sense of what services a particular healthcare organization have sold in a particular geographic region. While the only population represented in the data is the Medicare inpatient population, this dataset is generally regarded as sufficiently representative of the entire inpatient population to provide useful information.

Using embodiments of the invention described herein, it is also possible to use the MedPAR data to determine actual CPT-based pricing for a healthcare organization. "Actual," in this context, refers to the fact that the price was actually in fact charged by the healthcare organization—it is not, for example, an average of prices charged, which is a fictional value (i.e. the healthcare organization does not, in practice, actually charge the average amount). This actual pricing information may be helpful in rationalizing a healthcare organization's own chargemaster. It may also be helpful in analyzing a healthcare organization's chargemaster to make sure CPT codes are in line with market practices (for example, they are not "under" or "over" billing (billing rates less than/greater than the market, respectively).

FIG. 1 is a diagram that shows an exemplary embodiment of CPT pricing system 9, which includes pricing optimizer engine 11, common pricing engine 8, MedPAR database 15, and CPT price master database 16. In certain embodiments, CPT pricing system 9 may analyze a healthcare organization's chargemaster data, or a subset thereof, in light of data derived from MedPAR data. Particularly, CPT pricing system 9 may, in one embodiment, receive a healthcare organization's chargemaster, or a subset of their chargemaster, and then analyze it in light of MedPAR data to show where and how the healthcare organization's chargemaster differs from aspects of a competitor's or peer company. In addition, this analysis can be utilized by a healthcare organization to develop a transparent and defensible pricing structure. Further, this information may be useful for a healthcare organization interested in modifying its pricing, but unsure in what service areas it has the ability to make such modifications (i.e. in some service areas, it may have more or less ability to make changes, or risk being out of line with market conditions, for example). The information also may be useful for reports benchmarking a healthcare organization's book of business against other facilities selected to be peer comparables. Such benchmarking may additionally show service areas offered by a healthcare organization that fall outside of its desired market position. Such benchmarking may additionally show service areas offered by a healthcare organization that fall outside of its desired market position. For example, if a hospital is charging too high for cardiac-related procedures, a comparison against its peers will allow the hospital to establish a competitive posture. Similarly, the hospital may choose to keep its rates higher than the benchmarks because they may believe that their services are of a more specialized nature either because of volume, technology available at that hospital only, or other factors.

In one embodiment described herein, the CPT pricing system 9 is implemented in a computing device 14, which may be any computer with a memory, such as a personal computer, a server, multiple servers, or a personal digital assistant. For exemplary purposes only (and not limitation), computing device 14 is shown further containing user interface 12 and application program interface (API) 8. Computing device 14 is further showing including web server 3. A user, such as user 10, may interact with CPT pricing system 9 via user interface 12, or via web server 3 (via a web browser-type application running on a client computer). Web server 3, which shown in FIG. 1 as part of computing system 14, may be implemented in a variety of ways. For example, web server 3 might be on another computer system, such as stand alone computer system 5, and access the CPT pricing system via API 2. Users of the CPT pricing system, then, could interact with web server 3 running on stand alone computer system 5.

As mentioned, CPT pricing system 9, in the embodiment shown in FIG. 1, is comprised of pricing optimizer engine 11, common pricing engine 8, and two databases: MedPAR database 15, and CPT price master database 16. CPT pricing system 9 may be implemented in a variety of ways, and the manner in which a particular limitation discussed herein should not be read as limiting, because as one skilled in the art will appreciate, there are many ways to implement the system described herein. Common pricing engine 8 includes logic by which to "mine" MedPAR data, and populate CPT price master database 16. The mining operation functionally invoked by common pricing engine 8 in effect attempts to create chargemaster-like data for each facility represented in MedPAR, by applying a set of rules against the MedPAR data.

Or, to put it another way, common pricing engine 8 attempts to assign a most probable price to each CPT code a healthcare organization is charging for, using logic further discussed herein. Once CPT price master database 12 has been populated by common pricing engine 11, optimizer engine 11 facilitates interaction with CPT price master database 16. As a simplified example, if user 10 wanted to see what the price for a given CPT code was for a particular healthcare organization, user 10 may interact with user interface 12 to provide information including the CPT code of interest and the healthcare organization of interest (the target healthcare organization). This information would in turn be provided to optimizer engine, along with data representing the request itself. The information and request could be facilitated by, for example, a function call or similar. The optimizer engine 11, then, would make appropriate queries against CPT price master database 16, arrive at and possibly validate a result, then return it to user interface module 12, which in turn may present it to user 10. Alternatively, a similar interaction could be achieved where a user (not shown) interacts with web server 3 using a client computer running a web browser-type application. The two databases shown in CPT pricing system 9 may be implemented in a myriad of ways, as discussed further below.

CPT pricing system 9 receives MedPAR data, in one embodiment the location of which (usually a large flat file, but could be a database) is specified via user interface 12. User interface 12 may be a graphical user interface which facilitates data entry or uploading, and interfaces with common pricing engine 8 and optimizer engine 11. User 10 may be any person interested in accessing the functionality of CPT pricing system 9. If user 10 is an owner or administrator or manager of CPT pricing system 9, he may see a different set of user interface screens that particularly facilitate his management function. For example, user 10, if he is a manager of CPT pricing system 9, may access the common pricing engine 8 to load raw MedPAR data into MedPAR database 15, then invoke functionality within common pricing engine 8 to mine the MedPAR data from MedPAR database 15 and populate CPT price master database 16.

Alternatively or additionally, user 10 may, for example, be a consultant working for the benefit of a healthcare organization. In such a case, user 10 would typically not be concerned with interacting with CPT pricing system 9 in the same manner as a manager or administrator of the system. Instead, user 10 would access CPT pricing system, and particularly optimizer engine 11, via user interface 12 or web server 3. User 10 would submit queries to optimizer engine 11, which in turn would interact with CPT price master database 16 to return information or reports to user 10.

User 10 may also be a healthcare organization itself. Access in such a case would be via user interface 12, or via web server 3, or, if the healthcare organization has customized programs needing to access data of the type supplied by CPT pricing system 9, the healthcare organization may access the CPT pricing system via API 2.

Network 7 may be any network, public or private, that carries information. In FIG. 1, network 7 connects computing device 14, and thus CPT pricing system 9, to stand alone computer system 5. User 10 may interact with stand alone computer system 5, for example, if user 10 is not in physical proximity to computing device 14. Network 7 also connects to healthcare organization 4.

Computing device 14 may read software instructions from a computer-readable medium (such as a hard drive, a CD-ROM, or a computer memory), or may receive instructions from another source logically connected to computer, such as another networked computer. CPT pricing system 9 and/or any of the logic and procedures included herein may be embodied in a computer-readable medium, to be executed by a computer processor. Further, CPT pricing system 9 may be distributed to execute on multiple computers, and may be located remote to user 10 and accessible via a web browser or other interface. As mentioned earlier, computing device 14 typically includes hardware (not shown in FIG. 1) that may include one or more processors, volatile memory (RAM), a device for reading computer-readable media, and input/output devices, such as a display, a keyboard, and a pointing device. Computing device 14 may be, for example, a workstation, a laptop, a personal digital assistant (PDA), a server, a mainframe or any other general-purpose or application-specific computing device. Although not shown, computing device 14 may also include other software, firmware, or combinations thereof, such as an operating system and other application software. Computing device 14 may read executable software instructions from a computer-readable medium (such as a hard drive, or a CD-ROM), or may receive instructions from another source logically connected to computer, such as another networked computer. Further, components that comprise CPT pricing system 9 may be disparately located. For example, database components may be located in one geographic region, while processing components are located in another.

MedPAR database 15 and CPT price master database 16 may be any type of data stores. They need not be separate databases, and are shown as such for illustrative purposes only. The databases may be data storage files, or one or more database management systems (DBMS) executing on one or more database servers. The database management system may be a relational (RDBMS), hierarchical (HDBMS), multidimensional (MDBMS), object oriented (ODBMS or OODBMS) or object relational (ORDBMS) database management system. MedPAR database 15 and CPT price master database 16 are in one embodiment a single relational database such as SQL SERVER™ from Microsoft Corporation of Redmond, Wash.

Figure 2:
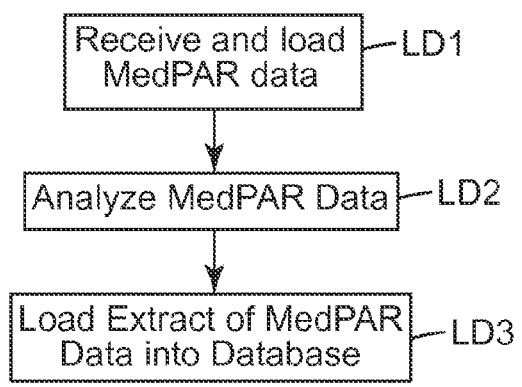
FIG. 2 is a high-level flowchart illustrating how MedPAR data is brought into and analyzed in accordance with the present invention.

FIG. 2 is a high-level flowchart illustrating how MedPAR data is brought into and analyzed by CPT pricing system 9. MedPAR data is received and loaded into MedPAR database 15 (LD1). This load may have minimal, if any, transformation associated with it—that is, the load is basically to get the raw MedPAR data into a database to allow subsequent manipulation. Next, the MedPAR data is analyzed (LD2) using exemplary techniques such as those further described below, specifically with respect to FIG. LD. Finally, the CPT price master database 16 is populated (LD3).

Figure 3:
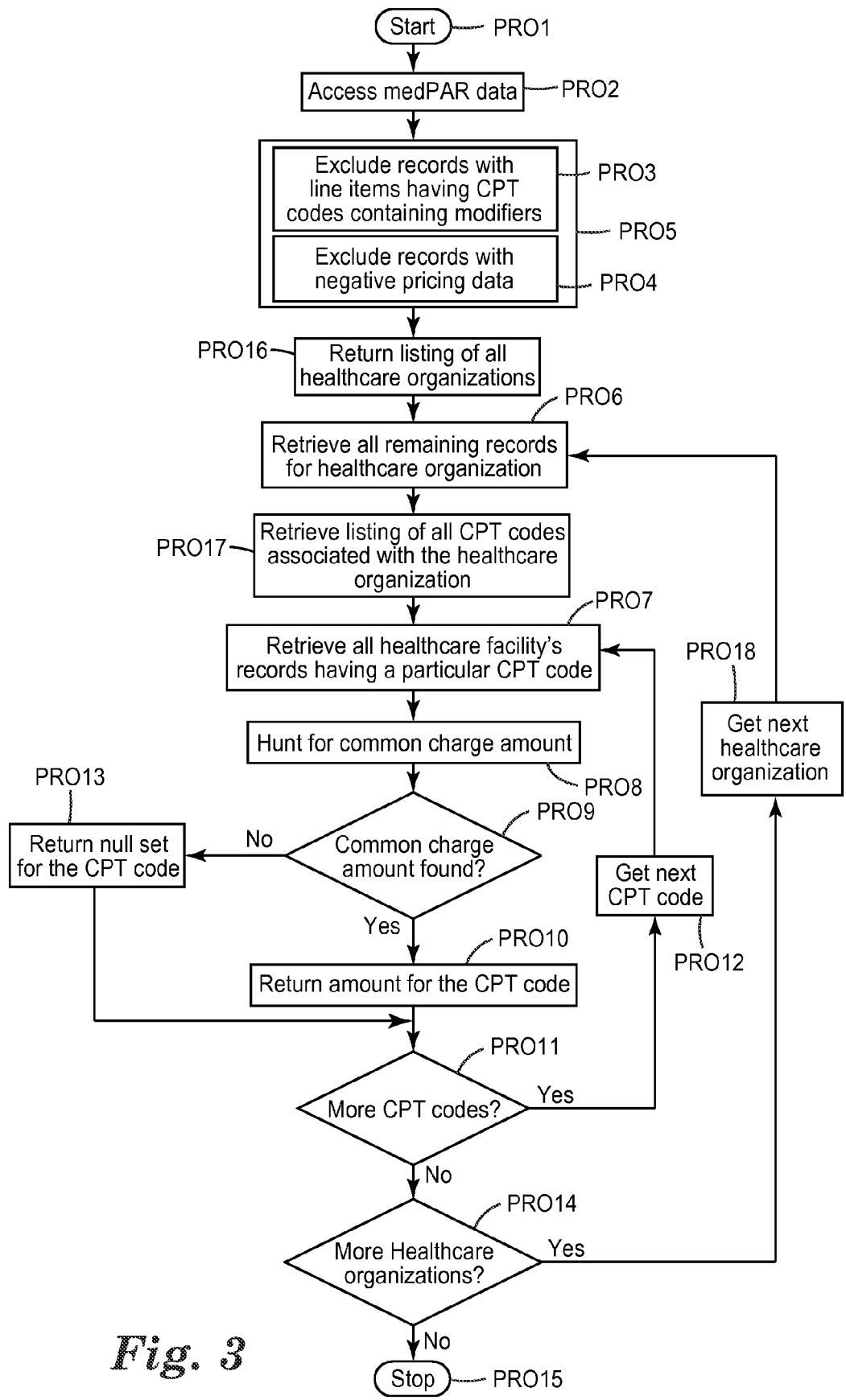
FIG. 3 is a flowchart graphically illustrating one embodiment of logic that could be used to populate a master database in accordance with the present invention.

FIG. 3 is a flowchart graphically illustrating one embodiment of logic that could be used in common pricing engine 8 to populate CPT price master database 16. In this particular embodiment of common pricing engine 8's logic, CPT price master database 16 is mined and populated in advance of optimizer engine 11 accessing it to fulfill user queries. One skilled in the art will appreciate MedPAR data could similarly be accessed and analyzed on the fly, with sufficient computing power. The batch-processing approach to analyzing MedPAR data disclosed in FIG. 3 should not be read as limiting, as one in the art will appreciate.

The data mining process starts (PRO1) by accessing MedPAR data (PRO2). The MedPAR data has already been loaded into a database such as MedPAR database 15. The MedPAR data is in raw form, comprised of records. Records contain claim information for a patient's visit to a healthcare organization. Records with CPT codes having certain modifiers that impact pricing are eliminated (PRO3). These records are eliminated because they may impact pricing. While many modifiers are informational (for example, a CPT code may describe a service associated with a broken arm, and the modifiers might further define which arm is broken (left or right)), another set (which is excluded) is not merely informational and instead may indicate other information about the procedure associated with the CPT code that does impact pricing. In one embodiment, the particular MedPAR modifiers excluded include those that could affect the pricing of the base code charge, or "code 5" as it is know to those skilled in the art. These may include, for example, 21, 22, 23, 26, 50, 51, 52, 53, 54, 55, 54, 62, 66, 75, 80, 81, 82, "TC" and "TU." Next, records with negative pricing data are excluded (PRO4). Particularly, records where charges are negative, or where charges less non-covered serves are negative. These data are excluded because they may represent duplicate claims, re-submissions of denied claims, or other out-of-the-ordinary type circumstances may have an undesirable bearing on the common price being sought. Steps illustrated in PRO3 and PRO4 are part of an initial culling of data represented in FIG. 3 as step PRO5. One skilled in the art will appreciate there may be other records for which it is advantageous to exclude, that could be a part of the initial culling. The two culling operations presented as part of culling operation PRO5 show just one manner, among many, whereby data could be prepared for analysis.

Next, a query is performed which returns of all healthcare organizations represented in the culled dataset (PRO16). A first healthcare organization is selected from the listing (PRO6) and analysis of that healthcare organization's billing practices begins. A listing of all CPT codes available for the healthcare organization is populated (PRO17). A first CPT code is selected for analysis, and all records associated with the particular healthcare organization are retrieved. These records include at least a CPT code and the amount charged for that CPT code. Other data is often included in these records.

Next, a routine applies logic to the listing of records having a common CPT code, to try to find a common charge amount (PRO8). This routine is further documented in FIG. 4. The hunt routine will either succeed in finding a charge amount for a given CPT code (YES at PRO9), or it will fail (NO at PRO9). If the routine fails to find a common charge amount, a null set or similar indicia is returned and associated with that CPT code (PRO13). If the routine succeeds in finding a common amount for the CPT code, the amount is returned and associated with that CPT code, for the particular healthcare organization, in CPT price master database 16. In either event, either a null (or similar) return value, or an actual price value is returned for a CPT code. Next, a check is made of the listing of CPT codes made in step PRO17. If there are more CPT codes in the listing (PRO11), the next code is chosen from the listing (PRO12) and the process of analyzing the particular CPT code for the healthcare organization repeats starting at step PRO7.

If there are no further CPT codes (NO at PRO11), the routine checks whether there are further healthcare organizations in the listing of healthcare organizations assembled in step PRO16. If there are (YES at PRO14), the next healthcare organization is retrieved (PRO18), and that organization's CPT codes and billing practices thereby analyzed (PRO6). If there are no further healthcare organizations, the routine completes (PRO15).

At this point, the CPT price master database 12 includes, for each healthcare organization, a listing of CPT codes that organization has attempted to bill for, and the a probable amount that represents the probable common charge associated with that CPT code (if such common charge was ascertainable by the hunt routine of PRO8).

Figure 4:
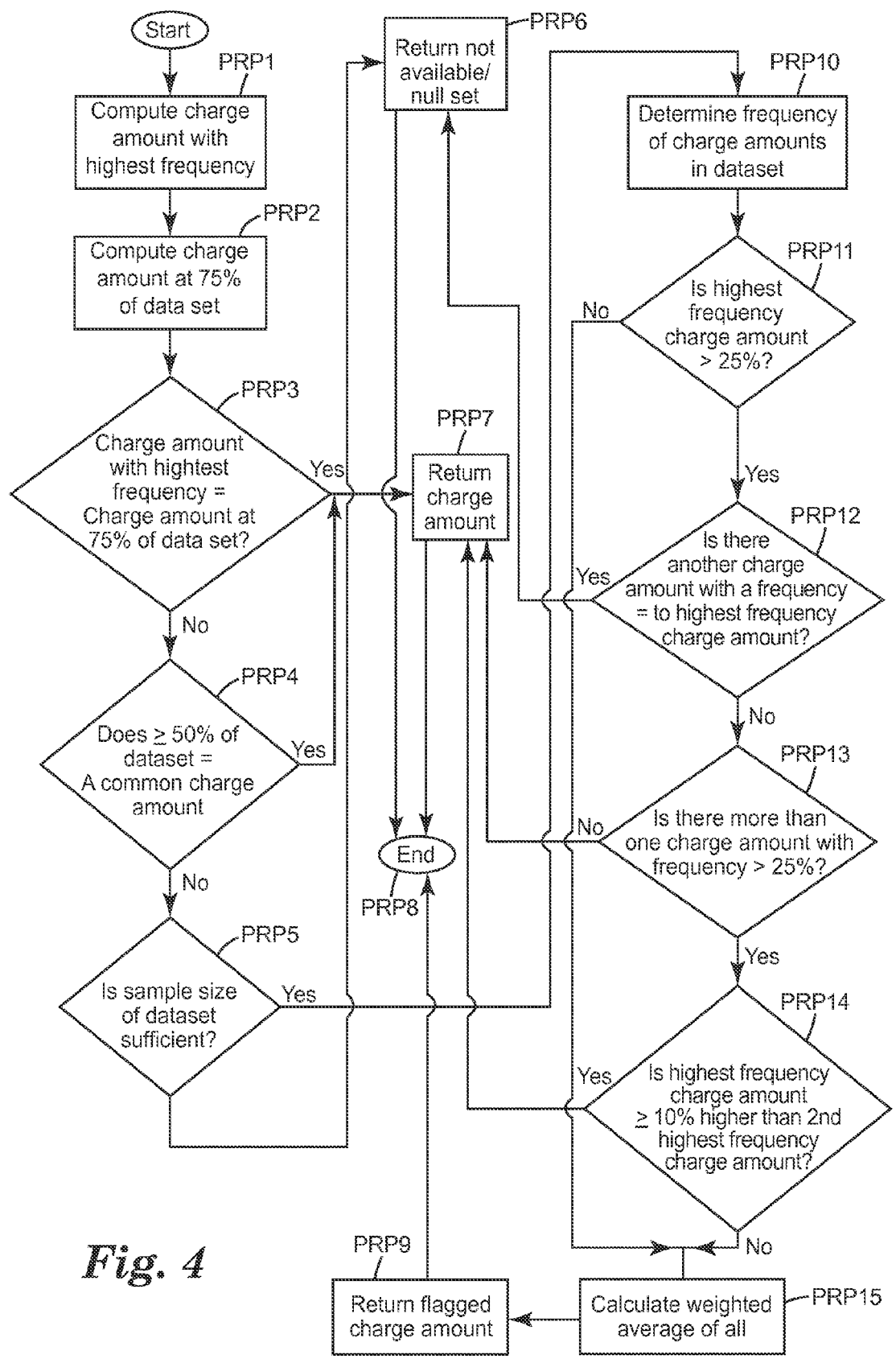
FIG. 4 is a functional diagram illustrating detail behind the hunt for common charge amount routine.

FIG. 4 is a functional diagram that illustrates detail behind the hunt for common charge amount of FIG. PRO, step PRO8. First, the charge amount with the highest frequency is computed (PRP1). Next, the charge amount at the $75^{th}$ percentile of the ranked dataset is computed (PRP2). The $75^{th}$ percentile is calculated to add significance to the data set. A comparison to the charge amount at the $75^{th}$ percentile assures that 75% of the charge values for a particular healthcare organization's CPT code have a common charge amount. A comparison of the charge amount with highest frequency (determined in PRP1) and the charge amount at $75^{th}$ percentile (determined is PRP2) is made. If the two charge amounts are equal (YES at PRP3) this charge amount is returned (PRP7). FIG. 5A is an exemplary table illustrating a simplified example of how this check in PRP3 may work. The CPT code for which a price is being sought is 11042. Count refers to the number of times a particular charge amount is associated with the CPT code in question. The charge amount with the highest frequency is $775 (would be computed in step PRP1). The charge amount at the $75^{th}$ percentile is also $775 (computed in step PRP2). The two values are compared in step PRP3, and as they are equal, the $775 value is assigned to CPT code 11042.

Returning to FIG. 4, if the two charge amounts are not equal (NO at PRP3), the routine checks whether 50% or more of the dataset is a common charge amount (PRP4). If it is (YES at PRP4), then that common charge amount is returned (PRP7). FIG. 5B is an example of the application of this rule to a simplified dataset. As in FIG. 5A, the routine is searching for a charge amount associated with CPT code 11042. In this example dataset, $775 has a frequency percentage (50%) at least equal to or greater than 50%. Thus, there would be a YES at PRP4, and the charge amount returned would be $775.

If there is not a common charge having 50% or more of the total number of entries in the dataset (NO at PRP4), a check is made of the total size of the dataset (PRP5). In one embodiment, this check involves checking whether the size of the dataset is >50. If the sample is of insufficient size (NO at PRP5), an appropriate return is made, for example "not available" or the null set (PRP6). If the sample is of sufficient size (YES at PRP5), the frequencies of each charge amount in the dataset is computed (PRP 10), along with the percentages of the total. For example, if a particular charge amount has a frequency of 2 out of a dataset size of 10, the percentage would be 20%. Next, a check is made to determine if the highest percentage amount is greater than 25%. If not, (NO at PRP11), the process proceeds to calculate weighted averages (PRP15), which will be described further later. If there is a frequency with a percentage >25%, the routine then checks if there is another charge amount with the same percentage as the highest one (PRP12). If there is, then "not available" or the null set is returned (PRP6). This is because there exists more than one charge amounts which could presumptively be the actual charge amount, and the routine does not have enough data to prefer one over the other. If there is not another charge amount with a frequency equal to the frequency of the highest charge amount (NO at PRP12), a check is made as to whether there is more than one charge amount with a frequency percentage greater than 25%. If there is no such charge amount with a frequency percentage greater than 25% (NO at PRP13), "not available" or the null set is returned (PRP6). If there is more than one charge amount having a frequency greater than 25% (YES at PRP13), the frequency percentage of the highest frequency charge amount is subtracted from the frequency percentage of the second highest frequency charge amount (PRP14). If this subtraction yields a number greater or equal to 10% (YES at PRP14), the higher charge amount is returned (PRP7). If the number is less than 10 (NO at PRP14), the weighted average charge price of the CPT code for the particular healthcare organization is calculated (PRP15), and this weighted average returned along with other indicia representing the result is flagged (PRP9). The result is flagged because it is an amount is not based on frequencies, and thus may not actually ever have been charged by the particular healthcare organization.

FIG. 5C, FIG. 5D, and FIG. 5E show examples of the application of the logic of shown in steps PRP10 through PRP14. The simplified datasets shown with respect to FIGS. 5C, 5D, and 5E would have progressed through logic shown preceding PRP10 (there would have been no computed common charge amount figured for these datasets). FIG. 5C shows a dataset having a highest frequency charge amount higher than 25% (YES to step PRP11 in FIG. 4). There is no other charge amount with a frequency equal to 25 (NO to step PRP12 in FIG. 4). Further, there is no other charge amount with a frequency greater than 25% (NO at step PRP13 in FIG. 4). Thus, charge amount $775 is returned (at step PRP7 in FIG. 4).

Turning to FIG. 5D, the example numbers show there is an amount having a frequency greater than 25% (YES at step PRP11 in FIG. 4). And there are in fact two numbers having the same charge amount frequency (the first for $775, the second for $985) (YES at step PRP12 in FIG. 4). Thus, a dataset synonymous with "not available" is found (step PRP6 in FIG. 4).

Turning to FIG. 5E, there are two charge amounts with a frequency above 25% of the total (YES at step PRP11 in FIG. 4, and NO at step PRP12 in FIG. 4). Since there is more than one charge amount with a frequency greater than 25% (YES at step PRP13), a check is made as to whether the difference in percentage between the frequencies of the two highest frequencies is at least 10%. Since in this case $775's 39% is 12 points greater than $985's 27%, and 12 is greater than 10 there is a YES at step PRP14 in FIG. 4, and the $775 charge amount is returned (step PRP7 in FIG. 4).

Figure 6:
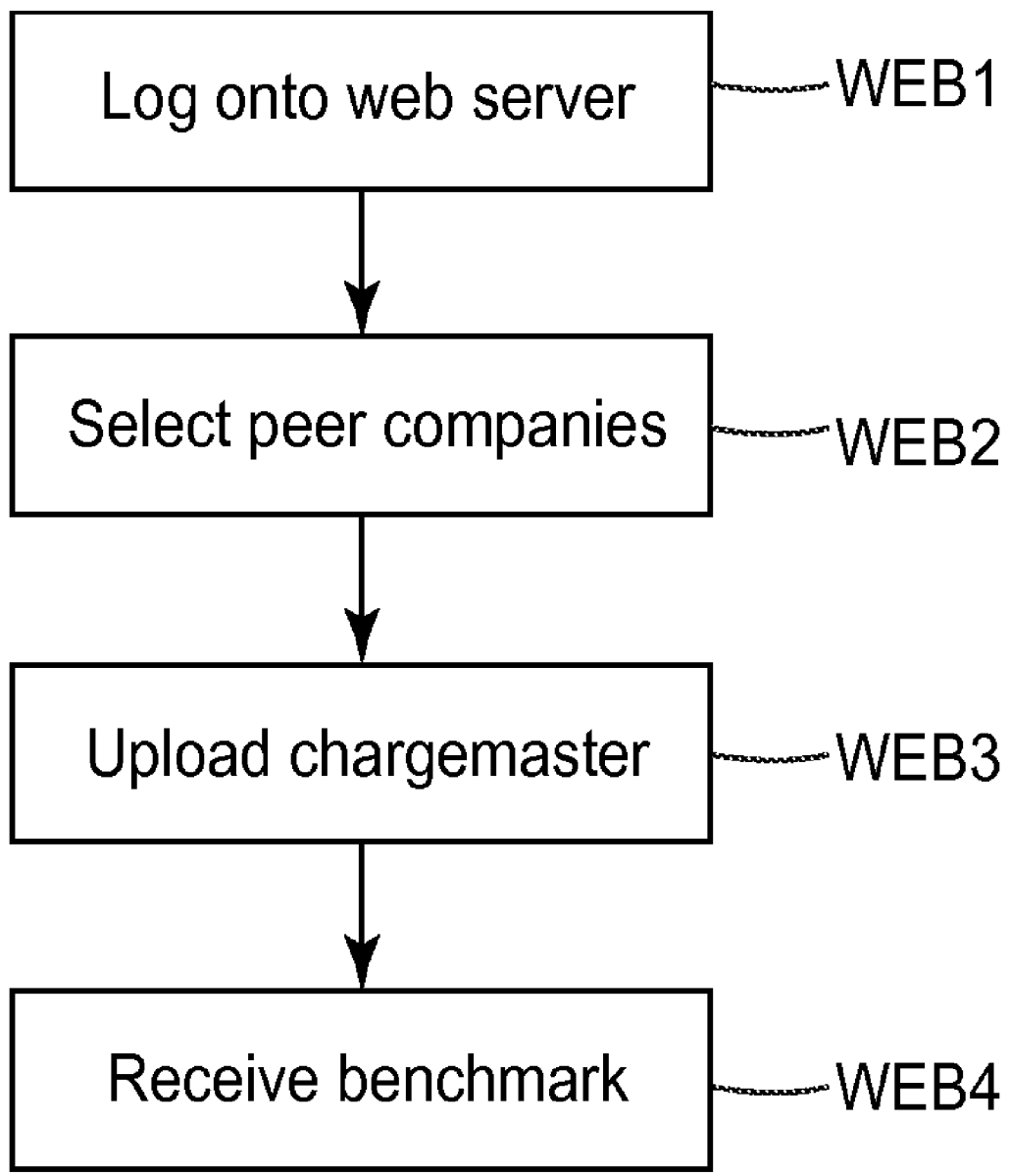
FIG. 6 is a flowchart showing one exemplary manner in which a user may interact with the system described herein.

FIG. 6 is a flowchart showing an exemplary manner in which user 10, who in this particular case is a consulting company, may interact with the CPT price master database 16, via optimizer engine 11, and in turn via one of the several interfaces into CPT pricing system (in this particular example web server 3). For the sake of example and not limitation, this process presumes CPT price master database 16 has already been populated using logic described above. One skilled in the art will recognize that the process and system could be architected to do CPT analysis of the type mentioned above real-time, and thus nullify the necessity of the CPT price master database. This is merely a system design consideration: where speed is paramount it may make sense to architect CPT pricing system 9 with CPT price master database 16 populated as an extract from MedPAR database 15. First, consultant logs onto web server 3 (WEB1). This may involve, for example, authentication. Next, a group of peer companies against which a particular healthcare organization (with respect to this FIG. this would be the customer) is to be analyzed is determined (WEB2). In one embodiment, an initial selection of peer companies is computed and suggested to user 10. The population of peer companies is determined based on the following criteria:

Geographical Area: Within an area (up to 60 mile radius) from the customer.

Bed Size: Facilities of similar bed size.

Revenue Size: Facilities that have a similar revenue.

Level of services: Compare facilities that perform similar services as the customer.

Once the peer companies have been selected, the customer's chargemaster, or germane portions of it (perhaps just a single CPT code), are uploaded to CPT pricing system 9. Analysis is done, and the consultant receives a benchmark report (WEB4) showing how the customer compares, in various aspects, to one or more peer companies.

Though described with respect to MedPAR data, the same or similar concepts described above could be applied to any data that defines multiple charge amounts charged for a particular procedure.

The foregoing description of various embodiments of the invention has been presented for the purposes of illustration and description. It is not intended to be exhaustive or to limit the invention to the precise form disclosed. Obvious modifications or variations are possible in light of the above teachings. The embodiment was chosen and described to provide the best illustration of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

All features and limitations presented in, or found to be in this application (including the claims), are intended to be open-ended limitations, unless the term 'consisting of' is explicitly used.

What is claimed is:

1. A computer-implemented method of determining an actual amount a target healthcare organization charges for a procedure, the procedure associated with a billing code, the method comprising:
    accessing, with a computer processor, billing data, from a database on a computer-readable medium, defining a plurality of charge amounts charged by the target healthcare organization for the procedure;
    applying, with the computer processor, a set of rules, from the computer-readable medium, to the billing data, wherein applying the set of rules further comprises computing a highest frequency charge amount, wherein the highest frequency charge amount of the plurality of charge amounts comprises a charge amount with the highest number of occurrences among the plurality of charge amounts; and,
    based on the application of the set of rules, selecting from the billing data using the computer processor, the highest frequency charge amount of the plurality of charge amounts, wherein the highest frequency charge amount comprises an actual dollar amount charged by the target healthcare organization for the procedure associated with the billing code; and
    generating, with the computer processor, a pricing structure of the target healthcare organization based on the actual dollar amount.

2. The method of claim 1, further comprising:
    receiving input defining the target healthcare organization.

3. The method of claim 2, further comprising:
    receiving input defining a CPT code.

4. The method of claim 1, wherein applying the set of rules comprises the steps of:
    computing whether a first charge amount has a frequency (among the plurality of charge amounts) that is greater than a threshold proportion and has the highest proportion of all of the charge amounts that comprise the plurality of charge amounts.

5. The method of claim 4, wherein the steps further comprise:
    computing whether a second charge amount has a frequency (among the plurality of charge amounts) that is greater than the threshold proportion and has the second highest proportion of alt of the charge amounts that comprise the plurality of charge amounts; and,
    computing whether the highest proportion is greater than the second highest proportion by a threshold amount.

6. The method of claim 1, wherein the dollar amount is provided to a competitor of the target healthcare organization.

7. The method of claim 1, wherein applying the set of rules comprises the steps of:
    a) computing a threshold charge amount, the threshold charge amount (of the plurality of charge amounts) being the charge amount at a threshold proportion of the plurality of charge amounts; and,
    b) comparing whether the highest frequency charge amount equals the threshold charge amount.

8. The method of claim 1,
    wherein the billing code further comprises a Current Procedure Terminology (CPT) code; and
    wherein the billing data further comprises Medicare Provider Analysis and Review (MedPAR) data.

9. A system for identifying an actual amount a target healthcare organization charged for a procedure, the procedure associated with a billing code, wherein the billing code comprises a Current Procedure Terminology (CPT) code, the system comprising:
    a database component, stored on a non-transitory computer-readable medium and executed by a processor, operative to maintain records identifying a plurality of charge amounts the target healthcare organization has charged for the procedure associated with the CPT code; and,
    the processor programmed to:
        retrieve the records from the database component;
        apply a set of rules to the records, wherein applying the set of rules further comprises computing a highest frequency charge amount, wherein the highest frequency charge amount of the plurality of amounts comprises a charge amount with the highest number of occurrences among the plurality of charge amounts; and,
        based on the application of the set of rules, select using the processor, the highest frequency charge amount of the plurality of charge amounts, wherein the highest frequency charge amount comprises an actual amount charged by the healthcare organization for the procedure associated with the billing code from plurality of amounts charged by the target healthcare organization for the procedure associated with the CPT code; and
        generate a pricing structure of the target healthcare organization based on the actual dollar amount.

10. The system of claim 9, wherein applying the set of rules comprises:
    a) determining a threshold charge amount, the threshold charge amount (of the plurality of amounts) being the charge amount at a threshold proportion of the plurality of charge amounts; and,
    b) comparing whether the highest frequency charge amount equals the threshold charge amount.

11. The system of claim 10, wherein applying the set of rules comprises:

determining whether a first charge amount has a frequency (among the plurality of amounts) that is greater than a threshold proportion and has the highest proportion of all of the amounts that comprise the plurality of amounts.

12. The method of claim 11, wherein the steps further comprise:
   determining whether a second charge amount has a frequency (among the plurality of amounts) that is greater than the threshold proportion and has the second highest proportion of all of the amounts that comprise the plurality of amounts; and,
   determining Whether the highest proportion is greater than the second highest proportion by a threshold amount.

13. The system of claim 9, further comprising:
   a user interface component operative to receive input from a user specifying the target healthcare organization, and to display the actual amount charged by the healthcare organization.

14. The system of claim 13, further comprising:
   a web server component operative to provide the user interface component to networked computers.

15. A computer-implemented method of benchmarking at least a portion of a first healthcare organization's chargemaster against a second healthcare organization, comprising:
   receiving, from a computer-readable medium, at least a portion of the first healthcare organization's chargemaster, the chargemaster including an amount charged for a procedure associated with a billing code, wherein the billing code comprises a Current Procedure Terminology (CPT) code:
   applying, with a computer processor, a set of rules to billing data, wherein the billing data comprises Medicare Provider Analysis and Review (MedPAR) data, the billing data, received from a database on the computer-readable medium, including data defining a plurality of amounts the second healthcare organization has charged for the procedure associated with the CPT code, the set of rules determining an actual charge amount, among the plurality of amounts, wherein applying the set of rules further comprises computing a highest frequency charge amount, wherein the highest frequency charge amount of the plurality of charge amounts comprises a charge amount with the highest number of occurrences among the plurality of charge amounts; and,
   providing a report to the first healthcare organization, the report including the amount charged by the first healthcare organization for the procedure associated with the CPT code compared against the actual charge amount charged by the second healthcare organization.

16. The method of claim 15, further comprising:
   modifying the first healthcare organization's chargemaster to be commensurate with the actual charge amount used by the second healthcare organization.

\* \* \* \* \*

UNITED STATES PATENT AND TRADEMARK OFFICE
CERTIFICATE OF CORRECTION

| | | |
|---|---|---|
| PATENT NO. | : 8,073,709 B2 | Page 1 of 1 |
| APPLICATION NO. | : 11/744556 | |
| DATED | : December 6, 2011 | |
| INVENTOR(S) | : Moreno et al. | |

It is certified that error appears in the above-identified patent and that said Letters Patent is hereby corrected as shown below:

Drawings
In the drawings, Sheet 3 of 6, Fig. 4, Box PRP3,
    delete "hightest" and insert -- highest -- therefor.

Column 5
Line 47-48, delete "below specifically with respect to FIG. LD."
    and insert -- below. -- therefor.

Column 6
Line 10, delete "is know to" and insert -- is known to -- therefor.

Column 7
Line 43, delete "(PRP 10)" and insert -- (PRP10) -- therefor.

Column 10
Claim 5, Line 9, delete "alt" and insert -- all -- therefor.
Claim 9, Line 53, delete "from plurality"
    and insert -- from the plurality -- therefor.

Column 11
Claim 12, Line 13, delete "Whether"
    and insert -- whether -- therefor.

Signed and Sealed this
Thirty-first Day of January, 2012

David J. Kappos
*Director of the United States Patent and Trademark Office*